United States Patent [19]  
Weitz, Jr. et al.

[11] 4,011,746  
[45] Mar. 15, 1977

[54] LIQUID DENSITY MEASUREMENT SYSTEM
[75] Inventors: Paul G. Weitz, Jr., Salisbury; David A. Lamphere, Milton, both of Vt.
[73] Assignee: Simmonds Precision Products, Inc., Tarrytown, N.Y.
[22] Filed: Feb. 2, 1976
[21] Appl. No.: 654,584
[52] U.S. Cl. ............................. 73/32 R; 324/61 R
[51] Int. Cl.² .................... G01N 9/00; G01R 27/26
[58] Field of Search ............ 73/30 R, 32 R, 61.1 R; 324/61 R

[56] References Cited
UNITED STATES PATENTS

| 3,421,077 | 1/1969 | Liu et al. ............................ 324/61 |
| 3,761,810 | 9/1973 | Fathaver ............................ 324/61 |
| 3,903,478 | 9/1975 | Stuart et al. ....................... 324/61 |

Primary Examiner—Herbert Goldstein  
Attorney, Agent, or Firm—Edwin E. Greigg

[57] ABSTRACT

A liquid density measurement system comprises a capacitance probe and a temperature sensor both immersible in a liquid the density of which is to be measured. Signals derived from the probe and sensor are converted into respective electrical signals representing changes in the dielectric constant and temperature of the liquid respectively. These signals are scaled in a predetermined mutual ratio and then summated to give an output signal proportional to the density of the liquid. The scaling ratio is set according to predetermined liquid parameters such that the accuracy of the density represented by the output signal is unaffected by changes in liquid composition.

11 Claims, 6 Drawing Figures

LIQUID DENSITY MEASUREMENT SYSTEM

BACKGROUND OF THE INVENTION

1. Field of the Invention

This invention relates to a method and system for measuring the density of liquids.

2. Description of the Prior art

There have been previously proposed liquid density measurement systems which are based on the theoretically predictable variation of dielectric constant of a non-polar liquid with changes in density of the liquid. Such a system may incorporate a capacitance probe to measure the dielectric constant of the liquid that occupies the space between plates of the probe. An a.c. signal is generated, the magnitude of which is proportional to the probe capacitance and thus to the value of the dielectric constant of the liquid. This a.c. signal is then processed in suitable circuitry to give an output signal representative of the liquid density for feeding, for example, to a digital display unit.

A drawback of such a system is that changes in the composition of the liquid under measurement gives rise to errors in the indicated density since, in general, the relationship between the liquid dielectric constant and liquid density will vary with liquid composition. Where the liquid under measurement is, for example, liquid natural gas (LNG) this drawback can be considerable since the composition of L.N.G. is variable over a wide range and may change due to boil off of certain fractions.

OBJECT AND SUMMARY OF THE INVENTION

It is an object of the invention to provide an improved liquid density measurement system.

SUMMARY OF THE INVENTION

It is a further object of the invention to provide a liquid density measurement system of high accuracy that can compensate for changes in liquid composition.

According to the invention there is provided a liquid density measurement system, comprising a capacitance probe mounted for immersion in a mass of liquid, the density of which is to be measured, the capacitance of the probe being dependent on the dielectric constant of the liquid, a capacitance converter unit connected to the probe and arranged to produce a first signal, the magnitude of which is dependent on the dielectric constant of the liquid, temperature sensing means mounted for immersion in the liquid and responsive to variations in temperature thereof, a temperature signal conditioning unit connected to the temperature sensing means and arranged to produce a second signal the magnitude of which is dependent on the temperature of the liquid, and a density computation unit connected to receive and individually scale said first and second signals, the computation unit including summing means arranged to sum the scaled first and second signals to produce an output signal proportional to the density of the liquid.

According to the invention there is also provided a method of measuring the density of a non-polar liquid comprising the steps of measuring changes in the dielectric constant of the liquid from a predetermined value and generating a first signal representative of said changes, measuring changes in the temperature of the liquid from a predetermined value and generating a second signal representative of said temperature changes, scaling said first and second signals by respective predetermined factors, and summing said scaled first and second signals together with a reference signal representative of a predetermined density, the resultant summation signal being directly proportional to the liquid density.

According to the invention there is further provided means responsive to variations in the dielectric constant of the liquid to produce a first signal proportional to said variations, temperature sensing means responsive to variations in temperature of the liquid to produce a second signal proportional to said temperature variations, and density computation means connected to receive, individually scale and add said first and second signals to produce an output signal proportional to the liquid density and independent of changes in composition of the liquid.

A liquid density measurement system embodying the invention will now be particularly described, by way of example, with reference to the accompanying diagrammatic drawings, in which:

DESCRIPTION OF THE PREFERRED EMBODIMENT

The liquid density measurement system to be described hereafter is particularly suited to density measurement of liquid mixtures such as liquid natural gas (LNG). L.N.G. consists primarily on non-polar hydrocarbons such as methane, ethane and propane, and nitrogen which is a non-polar inorganic element. L.N.G. thus follows established theory describing its response as a dielectric fluid in an electric field (the Clausiur-Mosotti Law) and the relationship between its dielectric constant K and density D can be expressed by the following equation:

$$(K - 1) = a D + b \qquad (1)$$

where $a$ and $b$ are constants.

Figure 1:
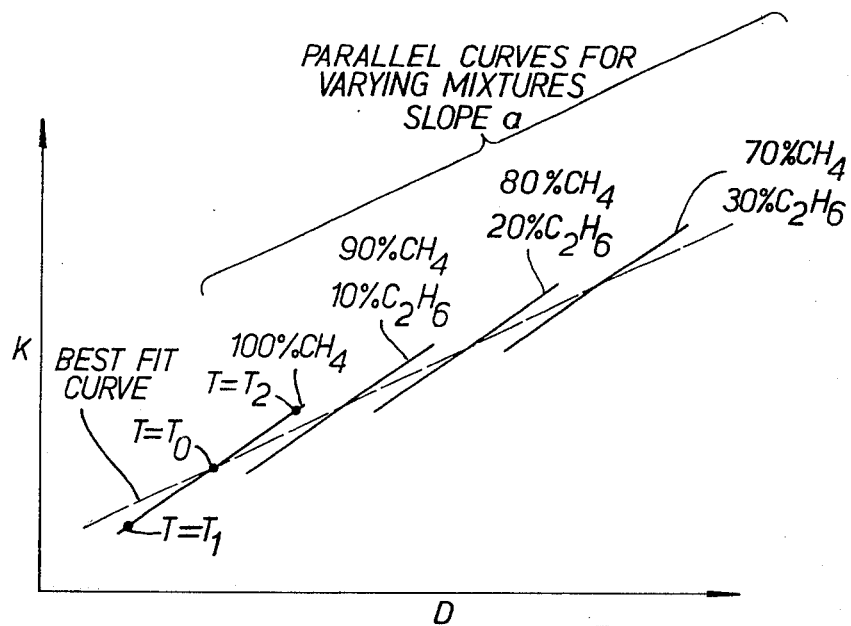
FIG. 1 is a graph of dielectric constant against density for different mixtures of liquid natural gas for use in explaining the operation of the system.

The value of the constant $b$ changes with variations in the composition of L.N.G. and plotting dielectric constant (K) against density (D) for different L.N.G. mixtures will give a series of parallel lines of slope $a$ (see FIG. 1). This has been shown both by test data and mathematical calculations. Similar results are obtained for liquid petroleum gas mixtures.

The temperature (T) of liquid under measurement varies along each curve as is indicated in FIG. 1 by the temperature points marked on one of the liquid mixture curves. It can also be seen from FIG. 1 that if the composition of the liquid mixture were constant, a liquid density measurement system could be set to provide a proportionality factor of $a$ between changes in dielectric constant and density. However, where the composition of the liquid mixture varies, errors in density measurement based solely on dielectric constant measurement will be produced. Setting up a liquid density measurement system to correspond to a "best fit" curve (dashed line, FIG. 1) for all mixes at all temperatures, while reducing the errors, will not eliminate them.

The liquid density measurement system to be described hereinafter incorporates a temperature sensor to sense the temperature of the liquid under measurement. Combination of the signal derived from the sensor with that obtained from the capacitance probe enables the system to compensate for liquid composition changes in a manner now to be described.

Figure 2:
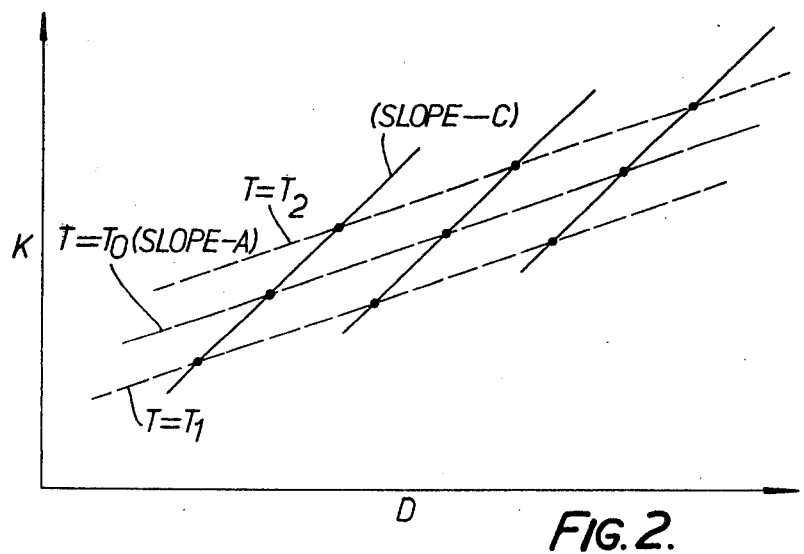
FIG. 2 ia a graph similar to FIG. 1 showing in dashed lines, curves of constant temperature.

Shown in FIG. 2 are a series of parallel dielectric constant vs density curves similar to those shown in FIG. 1, each curve corresponding to a particular liquid mixture and having a slope C equivalent to slope $a$ of FIG. 1. Constant temperature curves (dashed lines of slope A) have been drawn through the mixture curves. To obtain an accurate density reading for any liquid composition, first a measurement of the dielectric constant of the liquid mixture is used to give the liquid density assuming the liquid temperature were at a reference value $T_o$ (that is, D is read off from the line $T + T_o$ for a particular value of K), and then correction is made for any variation of liquid temperature from the reference temperature. For the straight line "curves" shown in FIG. 2, the density calculation is of the form $$D = D_o + A(K - K_o) + B(T - T_o) \qquad (2)$$

where $D = D_o + A(K - K_o)$ is the equation of the $T = T_o$ line $D_o$ = density at $K = K_o$ = predetermined constants B = function of difference between slope A and slope C An alternative form of this equation is $$D = D_o + A \Delta K + B \Delta T \qquad (3)$$

Figure 3:
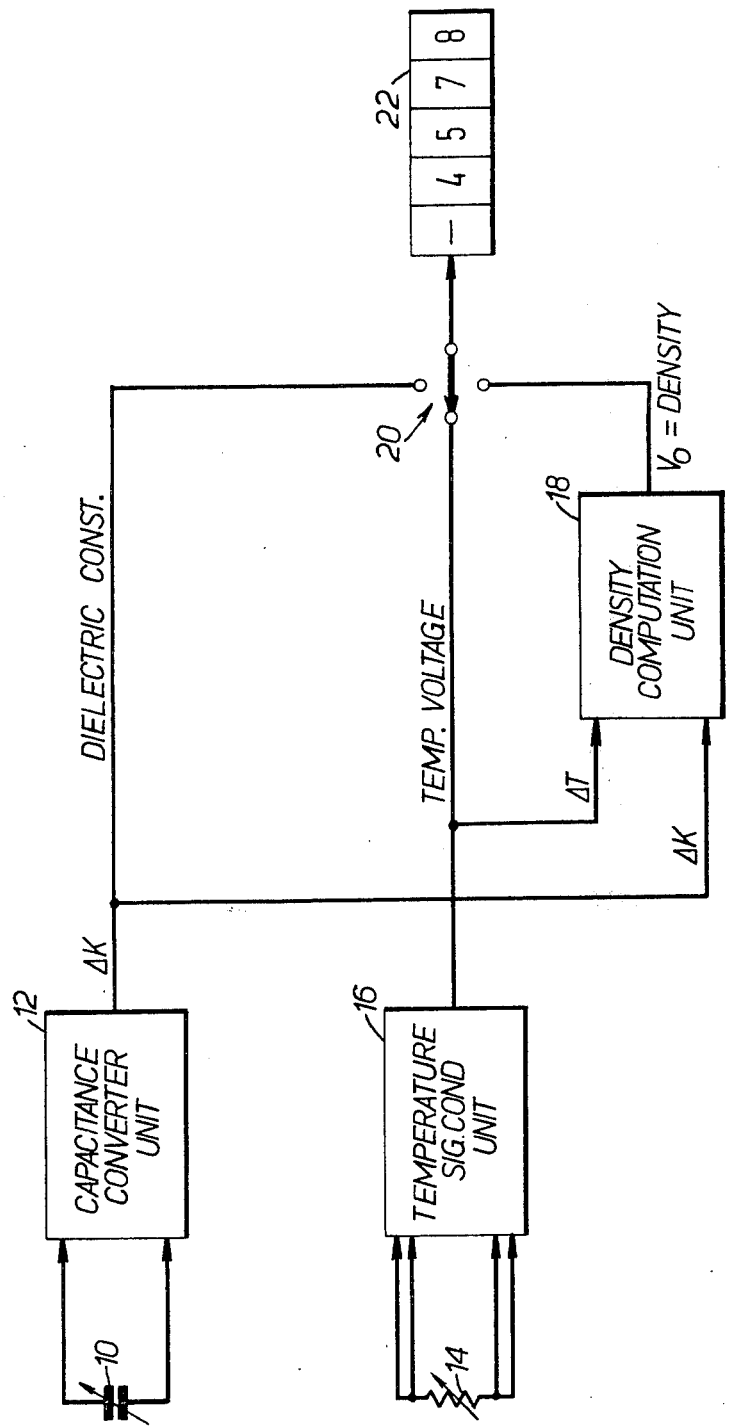
FIG. 3 is a block diagram of the system.

As shown in FIG. 3, the liquid density measurement system comprises a capacitance probe 10, (for example, in the form of two concentric tubes between which the liquid under measurement can pass), connected to a capacitance converter unit 12 which converts the a.c. signal across the capacitance probe 10 into a d.c. output signal proportional to $\Delta K$. The system further comprises a temperature sensor 14 (for example, a temperature dependent resistance immersed in the liquid) connected to a temperature signal conditioner unit 16 which produces a d.c. output signal proportional to T.

The outputs of the units 12 and 16 are fed to a density computation unit 18 which performs the various proportioning and summing functions necessary to execute equation (3) above. The output of the unit 18 is a d.c. voltage directly proportional to the liquid density. A select switch 20 enables the output of any one of the units 12, 16 or 18 to be displayed on a digital voltmeter display 22.

Figure 4:
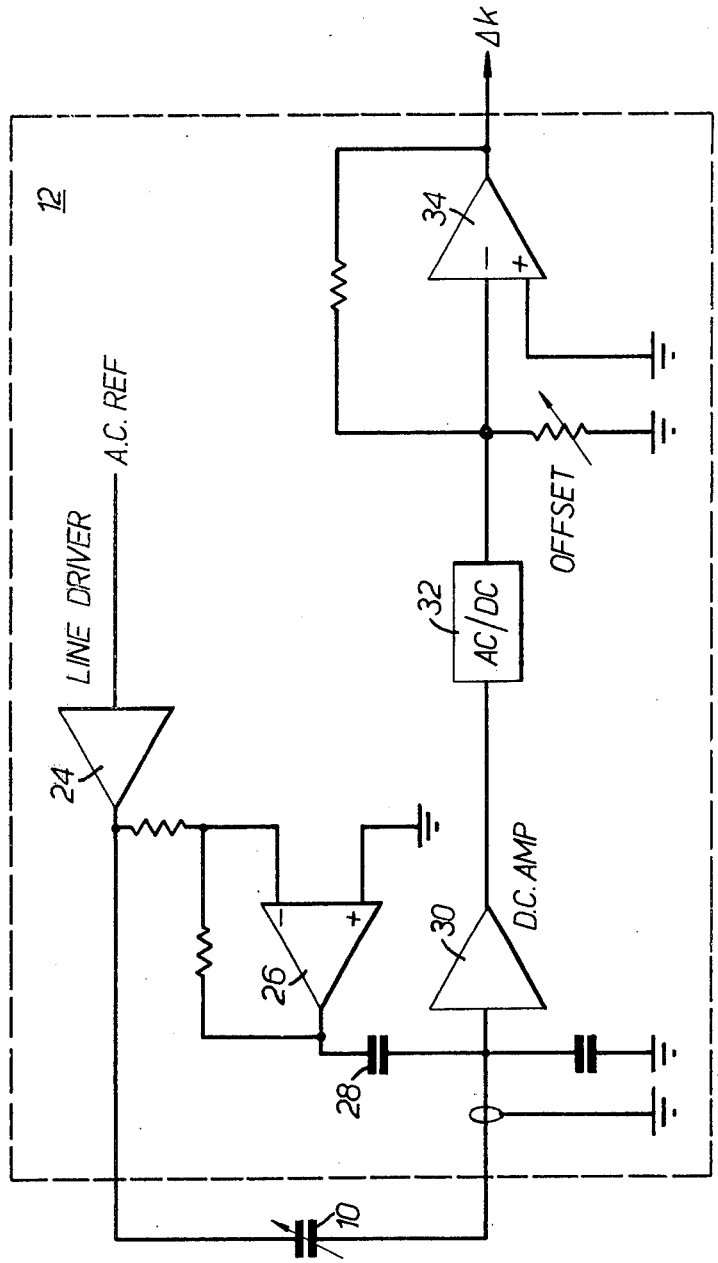
FIG. 4 is a circuit diagram of a capacitance converter unit of the system.

The capacitance converter unit 12 is shown in greater detail in FIG. 4 and comprises a line driver 24 which serves to amplify an a.c. reference signal to drive an a.c. current through the capacitance probe 10. The magnitude of the a.c. current is proportional to the capacitance of the probe and thus to the dielectric constant of the liquid under measurement. An inverter 26 (for example, an operational amplifier) drives a reference current, of inverse polarity to that passing through the probe 10, through a capacitor 28. The probe current and reference current are both fed to a summing input of an a.c. amplifier 30 where the reference current is subtracted from the probe current. The value of the capacitor 28 is selected to give such a magnitude of reference current that the a.c. voltage output signal of the amplifier 30 is directly proportional to changes in capacitance of the probe 10 and thus to changes in dielectric constant of the liquid. The a.c. voltage output signal of the amplifier 30 is fed to an A.C./D.C. converter 32, the output of which is connected to an amplifier 34. The amplifier 34 is provided with a voltage offset adjust capability to ensure that the d.c. voltage output signal is directly proportional to the change in dielectric constant.

Figure 5:
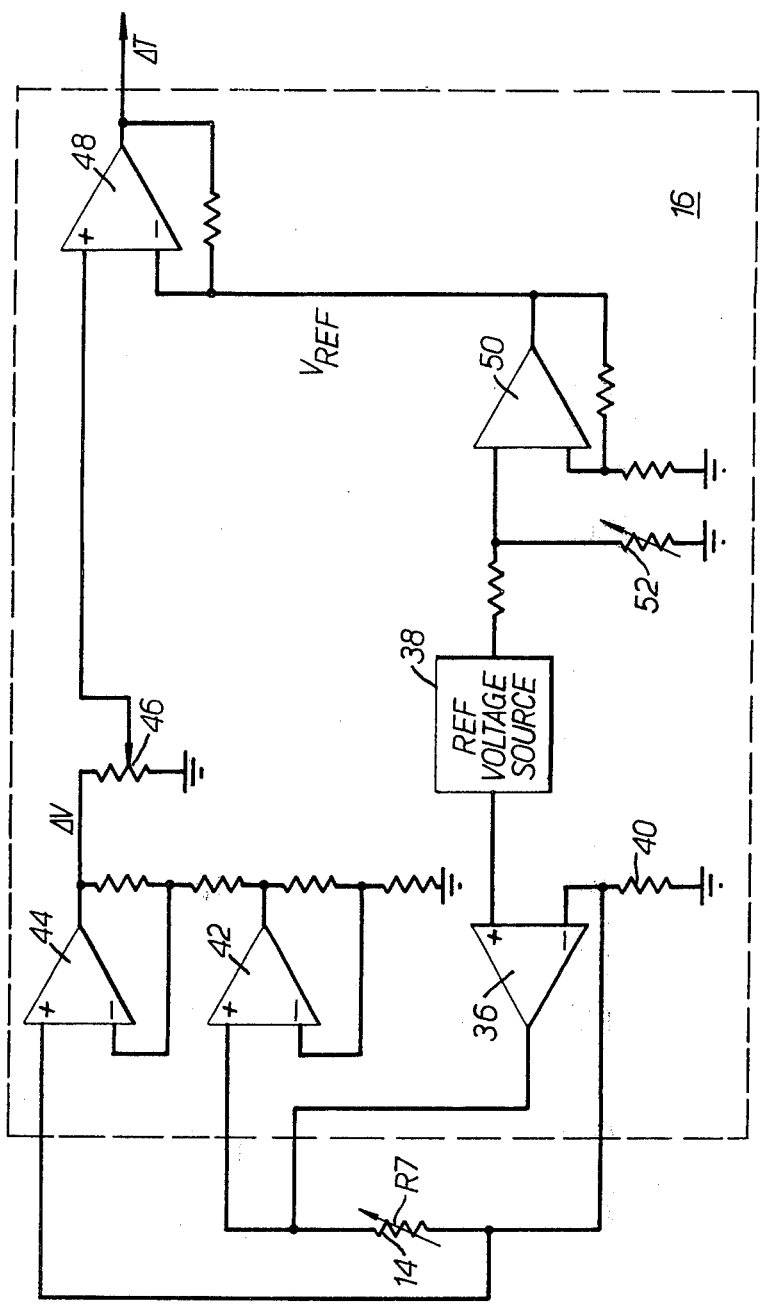
FIG. 5 is a circuit diagram of a temperature signal conditioner unit of the system.

The temperature signal conditioner unit 16 (FIG. 5) comprises a constant current source arranged to drive a constant current through the temperature sensor 14 (which, for example, takes the form of a platinum resistance). The constant current source is formed by an operational amplifier 36 which has its non-inverting input connected to receive a reference voltage from a reference voltage source 38 and its inverting input connected to sense the voltage drop across a standard resistor 40 connected in series with the sensor 14 but not immersed in the liquid. The amplifier 36 serves to maintain the voltage drop across the resistor 40 at a value set by the magnitude of the reference voltage fed to the non-inverting input of the amplifier 36, and this ensures that a constant current is driven through the sensor 14.

The voltages on each side of the sensor 14 are fed to operational amplifiers 42 and 44 respectively, and the outputs of these amplifiers are connected in a differential mode via a variable resistor 46 to the noninverting input of an operational amplifier 48. The signal fed to the non-inverting input of the amplifier 48 is therefore proportional to the voltage drop across the sensor 14 and thus proportional to the liquid temperature. A reference signal derived from the reference voltage source 38 via an operational amplifier 50, is fed to the inverting input of the amplifier 48. This reference signal is preset, using a variable resistor 52, to the value of the voltage drop present across the sensor 14 at the reference temperature $T_o$. The amplifier 48 serves to subtract the reference signal from the signal representing the actual voltage drop across the sensor 14. The signal appearing at the output of the amplifier 48 is thus directly proportional to the change in voltage drop across the sensor 14 and therefore is directly proportional to $\Delta T$, the change in liquid temperature from the reference temperature $T_o$.

Figure 6:
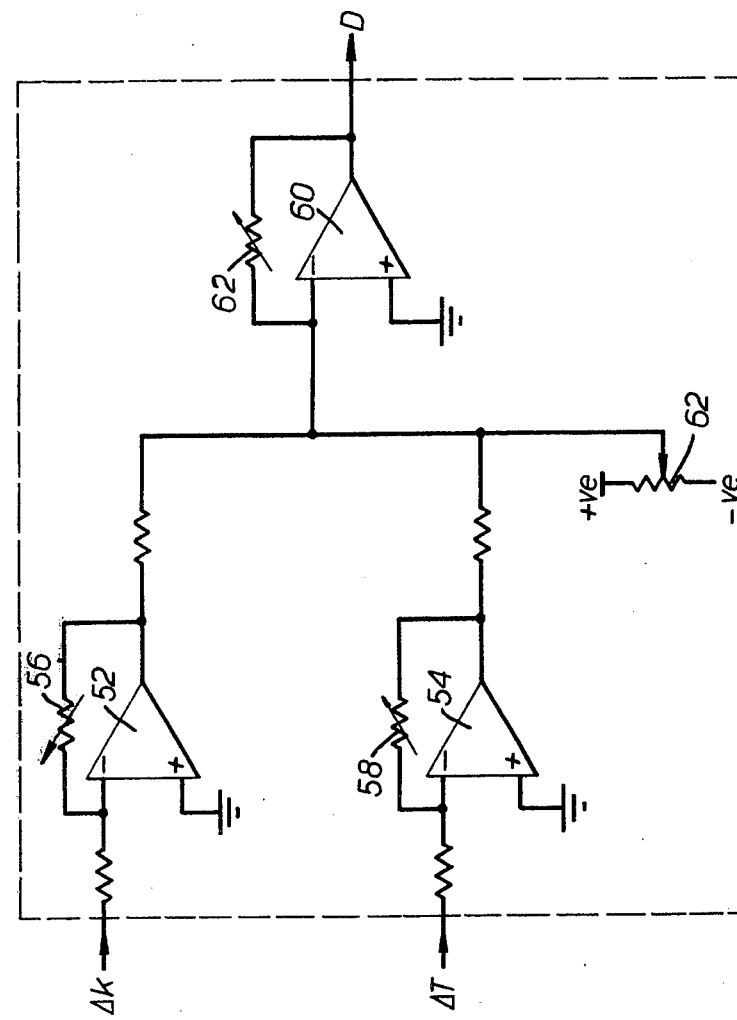
FIG. 6 is a circuit diagram of a density computation circuit of the system.

The density computation unit 18 (FIG. 6) comprises operational amplifiers 52 and 54, respectively, receiving the outputs of the units 12 and 16. The amplifiers 52 and 54 have respective variable feedback resistors 56 and 58 which serve to set the gain of the amplifiers. The resistors 56 and 58 are so adjusted that the signals representing the quantities $\Delta K$ and $\Delta T$ are proportioned by respective factors which are mutually in the same ratio as the factors A and B appearing in Equation (3).

The outputs of the amplifiers 52 and 54 are both connected to the inverting input of an operational amplifier 60 as is the slider of a variable resistor 62. The setting of the variable resistor 62 is such that the voltage appearing on its slider is proportional to the predetermined reference density $D_o$. The signals from the outputs of the amplifiers 52 and 54 and from the slider of the resistor 62 are summed at the inverting input of the amplifier 60 and the resultant signal produced at the output of the amplifier 60 is directly proportional to the density of the liquid, independently of its composition. The gain of the amplifier 60 is made variable by the provision of a variable resistor 62 in its feedback path and this enables the density signal to be scaled for compatability with the display 22.

The operational amplifiers in the described system can for example, be National Semiconductors LM 101A integrated circuits and the reference voltage source 38 can be formed around a Fairchild μA723 integrated circuit.

The described system can be provided with various additional features such as an alarm circuit responsive to an excessive liquid temperature being sensed, fail safe circuitry and zener barrier protection for the circuitry positioned adjacent the L.N.G.

The described system can be advantageously used for high accuracy measurement of liquid mixture densities in cases where a single valued function curve can be drawn through all the mixture (dielectric constant vs density) curves at a constant temperature point.

What is claimed is:

1. A liquid density measurement system, comprising:
   a capacitance probe mounted for immersion in a mass of liquid the density of which is to be measured, the capacitance of the probe being dependent on the dielectric constant of the liquid;
   a capacitance converter unit connected to the probe and arranged to produce a first signal the magnitude of which is dependent on the dielectric constant of the liquid;
   temperature sensing means mounted for immersion in the liquid and responsive to variations in temperature thereof;
   a temperature signal conditioning unit connected to the temperature sensing means and arranged to produce a second signal the magnitude of which is dependent on the temperature of the liquid; and
   a density computation unit connected to receive and individually scale said first and second signals, the computation unit including summing means arranged to sum the scaled first and second signals to produce an output signal proportional to the density of the liquid.

2. A system according to claim 1, wherein said density computation unit comprises first and second scaling means connected to receive said first and second signals respectively and adjustable to set their scaling factors in a ratio of X : Y, where X is the rate of change of dielectric constant with density of the liquid at constant temperature as the composition of the liquid varies, and Y is a function of the difference between said rate of change at constant temperature and the rate of change of dielectric constant with density for a fixed liquid composition as the temperature varies.

3. A system according to claim 1, wherein the density computation unit further includes means for generating a third signal of preset magnitude, representing a reference density, said summing means being connected to receive said third signal and to add the third signal to the scaled first and second signals whereby said output signal is directly proportional to the density of the liquid.

4. A system according to claim 1, wherein the density computation unit comprises first and second adjustable gain operational amplifiers connected to receive said first and second signals respectively whereby to scale said signals, said summing means comprising a third operational amplifier connected to receive the outputs of the first and second amplifiers.

5. A system according to claim 1, wherein the temperature sensing means comprises a temperature dependent resistance.

6. A system according to claim 5, wherein the temperature signal conditioning unit comprises:
   means operative to drive a predetermined current through the temperature dependent resistance;
   means connected across the temperature dependent resistance and operative to produce a temperature signal proportional to the voltage drop across the resistance when said predetermined current is being driven therethrough;
   means for generating a reference signal corresponding to the voltage drop across the temperature dependent resistance at a predetermined temperature; and
   means connected to receive said temperature and reference signals and operative to subtract the reference signal from the temperature signal to produce said second signal.

7. A system according to claim 1, wherein the capacitance converter unit comprises:
   means operative to drive an a.c. current through the probe;
   means for generating a reference a.c. current representative of a predetermined liquid dielectric constant;
   means connected to receive said probe and reference a.c. currents and operative to subtract the reference current from the probe current to produce an a.c. dielectric constant signal; and
   an A.C. to D.C. converter connected to receive and rectify said dielectric constant signal to produce said first signal.

8. A method of measuring the density of a non-polar liquid comprising the steps of:
   measuring changes in the dielectric constant of the liquid from a predetermined value and generating a first signal representative of said changes;
   measuring changes in the temperature of the liquid from a predetermined value and generating a second signal representative of said temperature changes,
   scaling said first and second signals by respective predetermined factors; and
   summing said scaled first and second signals together with a reference signal representative of a predetermined density, the resultant summation signal being directly proportional to the liquid density.

9. A method according to claim 8, comprising the steps of:
   measuring the rate of change of dielectric constant with density of the liquid at constant temperature as the composition of the liquid varies;
   measuring the rate of change of dielectric constant with density of the liquid for a fixed liquid composition as the temperature varies;
   deriving a difference function dependent on the difference between the said rate of change at constant temperature and the said rate of change at fixed liquid compositions; and
   setting said predetermined scaling factors for said first and second signals in a ratio corresponding to the ratio of said rate of change of dielectric constant at constant temperature to said difference function.

10. A system for measuring the density of a non-polar liquid, comprising:
   means responsive to variations in the dielectric constant of the liquid to produce a first signal proportional to said variations;
   temperature sensing means responsive to variations in temperature of the liquid to produce a second signal proportional to said temperature variations; and
   density computation means connected to receive, individually scale and add said first and second signals to produce an output signal proportional to the liquid density and independent of changes in composition of the liquid.

11. A system according to claim 10, wherein said density computation unit comprises first and second scaling means connected to receive said first and second signals respectively and adjustable to set their scaling factors in a ratio of X : Y, where X is the rate of change of dielectric constant with density of the liquid at constant temperature as the composition of the liquid varies, and Y is a function of the difference between said rate of change at constant temperature and the rate of change of dielectric constant with density for a fixed liquid composition as the temperature varies.

* * * * *